US012583873B2

(12) United States Patent
Lee

(10) Patent No.: US 12,583,873 B2
(45) Date of Patent: Mar. 24, 2026

(54) AMINO ACID MINERAL COMPLEX HAVING IMMUNOPOTENTIATING ACTIVITY AND COMPOSITION FOR FOODS, PHARMACEUTICALS, OR FEEDS COMPRISING SAME

(71) Applicant: BTN CO., LTD., Chungcheongnam-do (KR)

(72) Inventor: Byoung Ryol Lee, Chungcheongnam-do (KR)

(73) Assignee: BTN CO., LTD., Chungcheongnam-do (KR)

( * ) Notice: Subject to any disclaimer, the term of this patent is extended or adjusted under 35 U.S.C. 154(b) by 1147 days.

(21) Appl. No.: 17/262,149

(22) PCT Filed: Nov. 26, 2018

(86) PCT No.: PCT/KR2018/014575
§ 371 (c)(1),
(2) Date: Aug. 3, 2021

(87) PCT Pub. No.: WO2020/022575
PCT Pub. Date: Jan. 30, 2020

(65) Prior Publication Data

US 2021/0347788 A1 Nov. 11, 2021

(30) Foreign Application Priority Data

Jul. 25, 2018 (KR) ........................ 10-2018-0086355

(51) Int. Cl.

| | |
|---|---|
| ***C07F 3/06*** | (2006.01) |
| ***A23K 20/142*** | (2016.01) |
| ***A23K 20/24*** | (2016.01) |
| ***A23K 50/30*** | (2016.01) |
| ***A23L 33/175*** | (2016.01) |
| ***A23L 33/29*** | (2016.01) |
| ***A61K 31/198*** | (2006.01) |
| ***A61K 33/30*** | (2006.01) |
| ***A61K 39/12*** | (2006.01) |

(52) U.S. Cl.
CPC .............. *C07F 3/06* (2013.01); *A23K 20/142* (2016.05); *A23K 20/24* (2016.05); *A23K 50/30* (2016.05); *A23L 33/175* (2016.08); *A23L 33/29* (2016.08); *A61K 31/198* (2013.01); *A61K 33/30* (2013.01); *A61K 39/12* (2013.01)

(58) Field of Classification Search
CPC ......... C07F 3/06; A23K 20/142; A23K 20/24; A23K 50/30; A23L 33/175; A23L 33/29; A23L 33/165; A61K 31/198; A61K 33/30; A61K 39/12; Y02A 50/30; A61P 31/14; A61P 31/16; A61P 37/04
See application file for complete search history.

(56) References Cited

U.S. PATENT DOCUMENTS

| | | | |
|---|---|---|---|
| 3,899,521 A | 8/1975 | Evers | |
| 4,020,158 A | 4/1977 | Ashmead | |
| 4,167,564 A | 9/1979 | Jensen | |
| 4,216,143 A | 8/1980 | Ashmead | |
| 4,599,152 A | 7/1986 | Ashmead | |
| 4,721,644 A | 1/1988 | Mayo | |
| 4,725,427 A | 2/1988 | Ashmead | |
| 4,774,089 A | 9/1988 | Ashmead | |
| 4,830,716 A | 5/1989 | Ashmead | |
| 4,863,898 A | 9/1989 | Ashmead | |
| 6,166,071 A | 12/2000 | Ashmead | |
| 7,375,243 B2 | 5/2008 | Park | |
| 9,718,769 B2 | 8/2017 | Buisson | |
| 2004/0131643 A1* | 7/2004 | Grewal | A61K 39/107 424/643 |
| 2011/0117210 A1 | 5/2011 | Ugolkov | |
| 2012/0277306 A1 | 11/2012 | Park | |

FOREIGN PATENT DOCUMENTS

| | | |
|---|---|---|
| CN | 1467198 | 1/2004 |
| WO | 2008007868 A1 | 1/2008 |

OTHER PUBLICATIONS

Massa, M. B., Dalosto, S. D., Ferreyra, M. G., Labadie, G., & Calvo, R. Vibronic Behavior and Single-Crystal EPR Spectra of Cu(II) in Copper-Doped Diaqua(I-aspartato)zinc(II) Hydrate. J. Phys. Chem. A 1999, 103, 15, 2606-2617 (Year: 1999).*

Schubert, C., Guttek, K., Grüngreiff, K. et al. Oral zinc aspartate treats experimental autoimmune encephalomyelitis. Biometals 27, 1249-1262 (2014). (Year: 2014).*

Polatnick J, Bachrach HL. Effect of zinc and other chemical agents on foot-and-mouth-disease virus replication. Antimicrob Agents Chemother. May 1978; 13(5):731-4. (Year: 1978).*

Yin-Murphy M, Almond JW. Picornaviruses. In: Baron S, editor. Medical Microbiology. 4th edition. Galveston (TX): University of Texas Medical Branch at Galveston; 1996. Chapter 53. Available from: https://www.ncbi.nlm.nih.gov/books/NBK7687/ (Year: 1996).*

Massa et al. Vibronic Behavior and Single-Crystal EPR Spectra of Cu(II) in Copper-Doped Diaqua(laspartato)zinc(II) Hydrate. J. Phys. Chem. 1999, 103, 15, 2606-2617. (Year: 1999).*

Massa, et al., "Vibronic Behavior and Single-Crystal EPR Spectra of Cu(II) in Copper-Doped Diaqua(I-aspartato)zinc(II) Hydrate" J. Phys. Chem. A 1999, 103, 15, 2606-2617.

(Continued)

*Primary Examiner* — James H Alstrum-Acevedo
*Assistant Examiner* — Pierre Paul Eleniste
(74) *Attorney, Agent, or Firm* — DUANE MORRIS LLP; Gregory M. Lefkowitz; Brandon A. Chan

(57) ABSTRACT

The present invention relates to an amino acid mineral complex having immunopotentiating activity, and a composition for foods, pharmaceuticals, or feeds comprising the same. More particularly, the present invention relates to a composition for foods (or a food additive), pharmaceuticals, or feeds (or a feed additive) which comprises the amino acid mineral complex as an active ingredient so that it is possible to enhance the immunity of a human or an animal other than a human or increase the antibody production rate of an anti-virus vaccine.

6 Claims, 1 Drawing Sheet

(56) References Cited

OTHER PUBLICATIONS

Mariani, et al., “Effect of zinc supplementation on plasma IL-6 and MCP-1 production and NK cell function in healthy elderly: Interactive influence of 647 MT1a and −174 IL-6 polymorphic alleles”, Experimental Gerontology , 2008, vol. 43(5), p. 462-471.

Unknown Author, “Preparation and properties of zine amino acid,” China Academic Journal Electronic Publishing 1 House, 1994-2023; DOI:10.19500/j.cnki.0367-6358.1997.02.008.

* cited by examiner

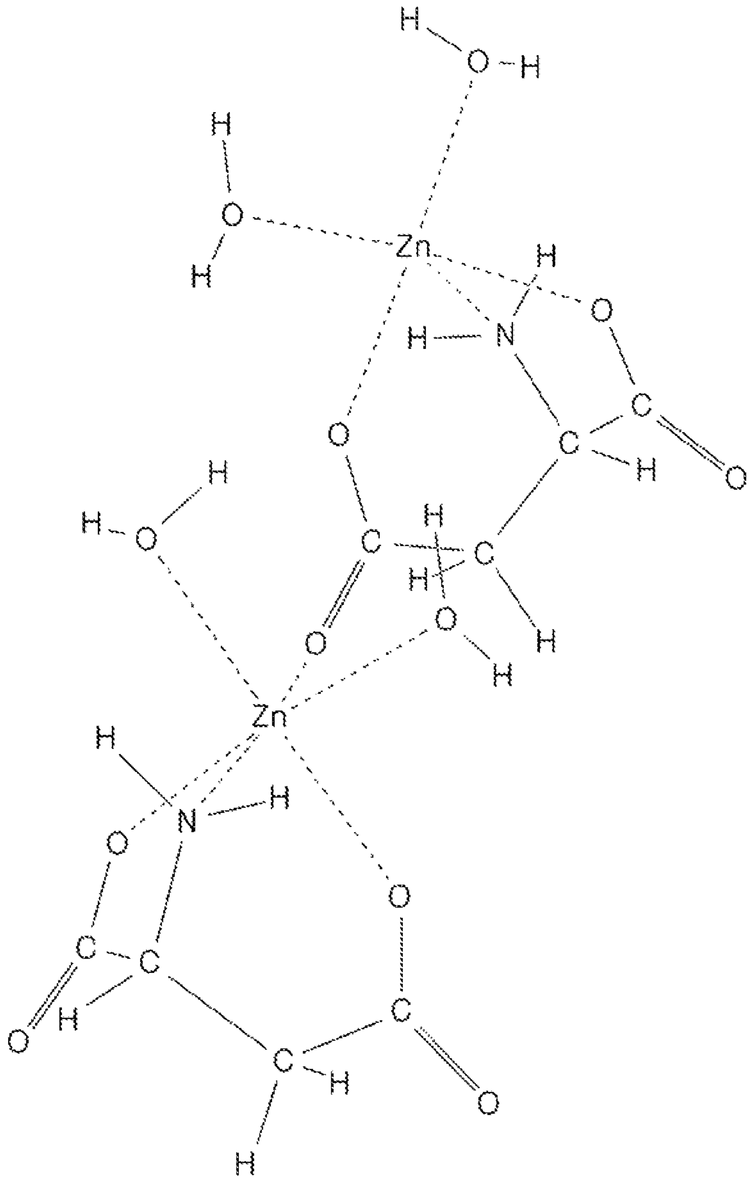

AMINO ACID MINERAL COMPLEX HAVING IMMUNOPOTENTIATING ACTIVITY AND COMPOSITION FOR FOODS, PHARMACEUTICALS, OR FEEDS COMPRISING SAME

CROSS-REFERENCE TO RELATED APPLICATIONS

This application is a § 371 national stage entry of International Application No. PCT/KR2018/014575, filed on Nov. 26, 2018, which claims priority to Korean Patent Application No. 10-2018-0086355, filed on Jul. 25, 2018, the entire contents of which are incorporated herein by reference.

TECHNICAL FIELD

The present disclosure relates to an amino acid-mineral complex having immunopotentiating activity and a composition for foods, pharmaceuticals or feeds containing the same. More particularly, the present disclosure relates to a composition for foods (or food additive), pharmaceuticals or feeds (or feed additive), which contains the amino acid-mineral complex as an active ingredient and is capable of enhancing the immunity of human or a non-human animal or increasing the antibody titer of an antiviral vaccine.

BACKGROUND ART

In mineral nutrition, the advantage of amino acid-mineral complexes is that they are easily absorbed by mucous cells or plant cells via active transport or other mechanisms. That is to say, absorption of minerals using amino acids as transport molecules is advantageous in that the problems associated with competition for active sites for absorption, inhibited absorption of special trace elements, etc. may be avoided. In general, the mineral-amino acid complexes are produced from the reaction between α-amino acids and metal ions. For the complex to have a ring structure, a metal ion having a valence of 2 or higher is required. In the reaction, the positive charge of the metal ion is neutralized by the negative charge of the amino group or carboxyl group of the α-amino acid.

There are a variety of literatures regarding the structure, chemical formula and bioavailability of the mineral-amino acid complexes. Representative examples include Ashmead et al., Chelated Mineral Nutrition, (1982), Chas. C. Thomas Publishers, Springfield, Ill., Ashmead et al., Intestinal Absorption of Metal Ions, (1985), Ashmead et al., Foliar Feeding of Plants with Amino Acid Chelates, (1986) and U.S. Pat. Nos. 4,020,158, 4,167,564, 4,216,143, 4,721,644, 4,599,152, 4,774,089, 4,830,716, 4,863,898, 4,725,427, etc.

REFERENCES OF RELATED ART

Patent Documents

U.S. Pat. No. 4,020,158.
U.S. Pat. No. 4,167,564.

Non-Patent Documents

Ashmead et al., Chelated Mineral Nutrition, (1982), Chas. C. Thomas Publishers, Springfield, Ill.
Ashmead et al., Intestinal Absorption of Metal Ions, (1985) Ashmead et al., Foliar Feeding of Plants with Amino Acid Chelates, (1986)

DISCLOSURE

Technical Problem

The present disclosure is directed to providing an amino acid-mineral complex having a novel chemical formula.

The present disclosure is also directed to providing a method for preparing the amino acid-mineral complex.

The present disclosure is also directed to providing a composition for enhancing immunological activity, which contains the amino acid-mineral complex.

Technical Solution

The present disclosure relates to an amino acid-mineral complex, which is a zinc aspartate hydrate of Chemical Formula 1 having a molecular formula $C_4H_9NO_7Zn$.

[Chemical Formula 1]

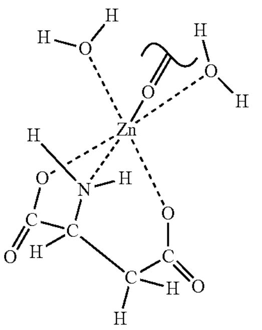

The zinc aspartate hydrate may be water-soluble. The expression water-soluble means that 1 g of the zinc aspartate hydrate is dissolved in 1-30 mL of water, specifically in 1-15 mL of water, at 25° C.

The amino acid-mineral complex may be for enhancing immunological activity.

The present disclosure also relates to a method for preparing the amino acid-mineral complex, which includes: a step of adding a zinc precursor and aspartic acid to water at a molar ratio of 1:0.8-2.5; and a step of heating the aqueous mixture solution of the zinc precursor and aspartic acid at 50-100° C. for 10 minutes to 24 hours.

The present disclosure also relates to a composition for enhancing immunological activity, which contains the amino acid-mineral complex as an active ingredient.

The composition for enhancing immunological activity may be a food composition, a food additive composition, a pharmaceutical composition, a feed composition or a feed additive composition.

The composition for enhancing immunological activity may be administered in combination with or sequentially with an antiviral vaccine.

The antiviral vaccine may be an avian vaccine for prevention of Newcastle disease, infectious bronchitis, coccidian diarrhea, avian pox, avian cholera, reovirus-induced tenosynovitis (viral arthritis), avian laryngotracheitis, avian encephalomyelitis, infectious bursal disease (IBD), Marek's disease, *Salmonella* infection, *Mycoplasma gallisepticum* infection, avian rhinotracheitis, avian herpes, *Mycoplasma hyopneumoniae* infection, egg drop syndrome, infectious coryza (*Haemophilus paragallinarum* infection), or *Mycoplasma synoviae* or avian reovirus infection;

a mammalian livestock vaccine for prevention or treatment of *Actinobacillus pleuropneumoniae* infection, atrophic rhinitis, pseudorabies, swine erysipelas, porcine parvovirus infection, enterotoxigenic *E. coli* infection, *Mycoplasma hyopneumoniae*, influenza infection, leptospira infection, *E. coli* infection, porcine reproductive and respiratory syndrome (PRRS), *Bordetella* and *multocida* A and D infection, *Haemophilus parasuis* infection, *Clostridium welchii* infection, rotavirus infection, *Streptococcus* infection, Glasser's disease, pneumonia, or *Bordetella bronchiseptica* infection; or a human vaccine for prevention of influenza, hepatitis A, hepatitis B, hepatitis C, herpes simplex virus (type 2) infection, poliomyelitis, diphtheria, pertussis, *Haemophilus influenzae* B (Hib) infection, measles, msumps, rubella, typhoid fever, varicella (chickenpox), dengue fever, Epstein-Barr virus infection, human papillomavirus infection, pneumococcus infection, *Micrococcus* infection, viral meningitis, rotavirus infection, tick-borne encephalitis, traveler's diarrhea, cholera, yellow fever, or tuberculosis.

Advantageous Effects

An amino acid-mineral complex of the present disclosure is water-soluble. It can dissolve quickly in water when formulated into a powder, a granule, a tablet such as an effervescent tablet, etc. and exhibits superior mineral absorption rate without precipitation when prepared into a liquid formulation.

In addition, a composition for enhancing immunological activity, which contains the amino acid-mineral complex of the present disclosure as an active ingredient, can enhance the immunity of human or a non-human animal or can increase the antibody titer of an antiviral vaccine.

In addition, the composition for enhancing immunological activity, which contains the amino acid-mineral complex of the present disclosure as an active ingredient, can decrease the feed amount required to achieve the same body weight gain when fed to a non-human animal by increasing feed efficiency and can increase body weight gain during the same period.

In addition, the composition for enhancing immunological activity, which contains the amino acid-mineral complex of the present disclosure as an active ingredient, exhibits an effect of remarkably reducing the emission of ammonia and hydrogen sulfide from manure. Therefore, it can be utilized, for human, as a deodorizing composition for abating fart smell or old person smell and, for non-human animals, especially for livestock such as cow, pig, etc., as a composition for abating the odor of a livestock manure to improve the environment of farmhouses.

BRIEF DESCRIPTION OF DRAWINGS

FIG. 1 schematically shows the coordinate bonding of aspartic acid (second aspartic acid) in zinc aspartate hydrate of Chemical Formula 1 with neighboring zinc aspartate hydrate.

BEST MODE

Hereinafter, the present disclosure is described in more detail.

The present disclosure relates to an amino acid-mineral complex, which is a zinc aspartate hydrate of Chemical Formula 1 having a molecular formula $C_4H_9NO_7Zn$.

[Chemical Formula 1]

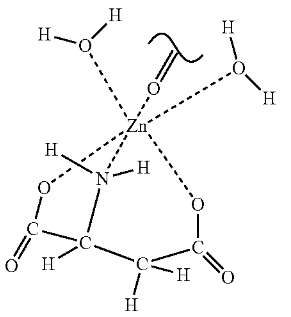

The zinc aspartate hydrate may be water-soluble. The expression water-soluble means that 1 g of the zinc aspartate hydrate is dissolved in 1-30 mL of water, specifically in 1-15 mL of water, at 25° C.

The amino acid-mineral complex may be for enhancing immunological activity.

The water-soluble amino acid-mineral complex may be prepared by a method including: a step of adding a zinc precursor and aspartic acid to water at a molar ratio of 1:0.8-2.5; and a step of heating the aqueous mixture solution of the zinc precursor and aspartic acid at 50-100° C. for 10 minutes to 24 hours.

The present disclosure relates to a composition for enhancing immunological activity, which contains the amino acid-mineral complex as an active ingredient.

The zinc precursor may be a zinc salt or a zinc oxide that may be used as a food, pharmaceutical or feed. Specifically, a water-soluble zinc salt such as zinc gluconate or zinc sulfate or water-insoluble zinc oxide with proven safety as a food additive may be used. More specifically, zinc oxide has excellent activity of increasing the antibody titer of an antiviral vaccine. Although it has been formerly taken for granted that a water-soluble zinc salt is used in the preparation of a zinc-aspartic acid complex, it has been found out that a zinc-aspartic acid complex with better efficacy is formed by using a water-insoluble zinc oxide and conducting heating at specific temperature for specific time.

The molar ratio of the zinc precursor and aspartic acid refers to the molar ratio of zinc and aspartic acid. The molar ratio may be 1:0.8-2.5, specifically 1:1.5-2.2. Although the theoretical molar ratio of zinc and aspartic acid in the zinc aspartate hydrate of Chemical Formula 1 is 1:2, the water-soluble zinc aspartate hydrate may be formed more easily when the aspartic acid is added in excess of the zinc precursor.

The heating step may be performed at 50-100° C. for 10 minutes to 24 hours. Although, for a water-soluble zinc salt, the reaction may be completed by heating at a relatively lower temperature for a shorter time, e.g., at 50-80° C. for 10 minutes to 1 hour, for a zinc oxide, it is preferred that the heating is performed at 80-100° C. for 1 hour or longer, specifically for 1.5 hours. Meanwhile, for both the water-soluble zinc salt and the zinc oxide, since about 95%, specifically 99% or more, of aspartic acid reacts within 3 hours, the decrease in insoluble or unreacted material may not be large even when the heating time exceeds 3 hours. During the heating step, ultrasonication may be used to reduce the reaction time.

The method may further include a step of removing insoluble material from the reaction solution. Although the step of removing the insoluble material may be added when a water-soluble zinc salt is used as the zinc precursor, it may be more necessary when a zinc oxide is used as the zinc precursor.

The step of removing the insoluble material may be performed by filtration using submicrometer, e.g., 0.2 μm, filter paper or filter cloth, and the insoluble material may be removed through centrifugation prior to or separately from the filtration.

The preparation method is advantageous over the existing preparation method of a zinc-aspartic acid complex in that no additional additive is necessary other than the zinc precursor, aspartic acid and water, and the process cost is saved because the preparation process is simple.

In the present disclosure, the expression 'as an active ingredient' means that the mineral-amino acid complex of the present disclosure is contained in an amount enough to achieve the desired effect or activity. In a specific exemplary embodiment of the present disclosure, a food composition, a pharmaceutical composition or a feed composition of the present disclosure contains the mineral-amino acid complex in an amount of, for example, 0.001 mg/kg or more, specifically 0.1 mg/kg or more, more specifically 10 mg/kg or more, further more specifically 100 mg/kg or more, even more specifically 250 mg/kg or more, most specifically 0.1 g/kg or more. The food additive composition or the feed additive composition may contain the mineral-amino acid complex in an amount of 10 g/kg or more, specifically 50 g/kg or more, more specifically 100 g/kg or more, and may consist only of the mineral-amino acid complex.

The pharmaceutical composition of the present disclosure includes, not only a pharmaceutical composition for human, but also a veterinary pharmaceutical composition for a non-human animal such as a bird or a mammal. The pharmaceutical composition may be prepared by using, in addition to the active ingredient, a pharmaceutically suitable and physiologically acceptable adjuvant. As the adjuvant, an excipient, a disintegrant, a sweetener, a binder, a coating agent, a swelling agent, a lubricant, a glidant, a flavorant, etc. may be used.

The pharmaceutical composition may be administered in combination with or sequentially with an antiviral vaccine. For this, the pharmaceutical composition of the present disclosure may be formulated together with or independently of the antiviral vaccine.

The antiviral vaccine may be an avian vaccine for prevention of Newcastle disease, infectious bronchitis, coccidian diarrhea, avian pox, avian cholera, reovirus-induced tenosynovitis (viral arthritis), avian laryngotracheitis, avian encephalomyelitis, infectious bursal disease (IBD), Marek's disease, *Salmonella* infection, *Mycoplasma gallisepticum* infection, avian rhinotracheitis, avian herpes, *Mycoplasma hyopneumoniae* infection, egg drop syndrome, infectious coryza (*Haemophilus paragallinarum* infection), or *Mycoplasma synoviae* or avian reovirus infection; a mammalian livestock vaccine for prevention or treatment of *Actinobacillus pleuropneumoniae* infection, atrophic rhinitis, pseudorabies, swine erysipelas, porcine parvovirus infection, enterotoxigenic *E. coli* infection, *Mycoplasma hyopneumoniae*, influenza infection, leptospira infection, *E. coli* infection, porcine reproductive and respiratory syndrome (PRRS), *Bordetella* and *multocida* A and D infection, *Haemophilus parasuis* infection, *Clostridium welchii* infection, rotavirus infection, *Streptococcus* infection, Glasser's disease, pneumonia, or *Bordetella bronchiseptica* infection; or a human vaccine for prevention of influenza, hepatitis A, hepatitis B, hepatitis C, herpes simplex virus (type 2) infection, poliomyelitis, diphtheria, pertussis, *Haemophilus influenzae* B (Hib) infection, measles, msumps, rubella, typhoid fever, varicella (chickenpox), dengue fever, Epstein-Barr virus infection, human papillomavirus infection, pneumococcus infection, *Micrococcus* infection, viral meningitis, rotavirus infection, tick-borne encephalitis, traveler's diarrhea, cholera, yellow fever, or tuberculosis.

The pharmaceutical composition may be formulated by using one or more pharmaceutically acceptable carrier in addition to the above-described active ingredient.

The pharmaceutical composition may be formulated in the form of a granule, a powder, a tablet, a coated tablet, a capsule, a suppository, a liquid, a syrup, a juice, a suspension, an emulsion, a medicinal drip, an injectable, etc. For example, in order to formulate the composition into a tablet or a capsule, the active ingredient may be combined with an oral, nontoxic, pharmaceutically acceptable inert carrier such as ethanol, glycerol, water, etc. Also, if desired or necessary, a suitable binder, lubricant, disintegrant or colorant or a mixture thereof may also be included. Suitable binders include, but are not limited to, natural sugars such as starch, gelatin, glucose or β-lactose, natural or synthetic gums such as corn sweetener, acacia, tragacanth or sodium oleate, sodium stearate, magnesium stearate, sodium benzoate, sodium acetate, sodium chloride, etc. Disintegrants include, but are not limited to, starch, methyl cellulose, agar, bentonite, xanthan gum, etc.

A composition formulated into a liquid solution may contain, as a pharmaceutically acceptable carrier, one or more of saline, sterile water, Ringer's solution, buffered saline, albumin injection, dextrose solution, maltodextrin solution, glycerol and ethanol, which are biocompatible and suitable for sterilization. If necessary, other common additives such as an antioxidant, a buffer, a bacteriostat, etc. may be added. In addition, a diluent, a dispersant, a surfactant, a binder and a lubricant may be further added to formulate the composition into an injectable formulation such as an aqueous solution, a suspension, an emulsion, etc., a pill, a capsule, a granule or a tablet.

Specifically, the formulation may be prepared depending on the particular disease or ingredients using the methods described in Remington's Pharmaceutical Science (Mack Publishing Company, Easton Pa.).

The pharmaceutical composition of the present disclosure may be administered orally or parenterally. The parenteral administration may be carried out by intravenous injection, subcutaneous injection, intramuscular injection, intraperitoneal injection, transdermal administration, etc. Specifically, the administration may be carried out by oral administration.

An adequate administration dosage of the pharmaceutical composition of the present disclosure varies depending on various factors such as formulation method, administration method, the age, body weight, sex, pathological condition and diet of a patient or an animal, administration time, administration route, excretion rate and response sensitivity. An ordinarily skilled physician or veterinarian can easily determine and prescribe an administration dosage effective for desired treatment or prevention. According to a specific exemplary embodiment of the present disclosure, a daily administration dosage of the pharmaceutical composition of the present disclosure is 0.001-10 g/kg.

The pharmaceutical composition of the present disclosure may be prepared into a unit-dose form by formulating using a pharmaceutically acceptable carrier and/or excipient or may be introduced into a multi-dose container according to a method that can be easily executed by those having ordinary knowledge in the art to which the present disclosure belongs. The formulation may be in the form of a solution in an oil or an aqueous medium, a suspension, an emulsion, an extract, a powder, a granule, a tablet or a capsule, and may further contain a dispersant or a stabilizer.

The term "effective amount" used herein refers to an amount of the active ingredient or the pharmaceutical composition which induces biological or medical response expected by a researcher, a veterinarian, a physician or a clinician in tissues, animals or humans, and includes an amount which induces alleviation of the symptoms of a particular disease or disorder. It is obvious to those skilled in the art that the effective amount and number of administration of the active ingredient of the present disclosure will vary depending on the desired effect. Therefore, the optimum administration dosage may be easily determined by those skilled in the art, and may be modified depending on various factors including a particular disease, the severity of the disease, the contents of the active ingredient and other ingredients contained in the composition, formulation type, the age, body weight, general health condition, sex and diet of a patient or an animal, administration time, administration route, excretion rate, treatment period, and drugs used in combination. In the method for prevention, treatment or improvement of the present disclosure, the mineral-amino acid complex may be administered at a dosage of 0.001 mg/kg to 10 g/kg based on adults, once or several times a day.

The food composition or food additive composition according to the present disclosure may be formulated in the same manner as the pharmaceutical composition and may be used as a functional food or may be added to various foods. Examples of the food to which the food additive composition may be added include beverages, alcoholic beverages, confectionery, diet bars, dairy products, meat, chocolate, pizza, ramyeons, other noodles, gums, ice creams, vitamin complexes, dietary health supplements, etc.

The food composition of the present disclosure may contain, in addition to the mineral-amino acid complex as the active ingredient, ingredients commonly added when preparing foods. Examples include a protein, a carbohydrate, a fat, a nutrient, a seasoning agent and a flavorant. Examples of the carbohydrate include common sugars such as monosaccharides, e.g., glucose, fructose, etc., disaccharides, e.g., maltose, sucrose, oligosaccharides, etc. and polysaccharides, e.g., dextrin, cyclodextrin, etc. and sugar alcohols such as xylitol, sorbitol, erythritol, etc. As the flavorants, natural flavorants [thaumatin, stevia extract (e.g., rebaudioside A, glycyrrhizin, etc.)] or synthetic flavorants (saccharin, aspartame, etc.) may be used. For example, when the food composition of the present disclosure is prepared into a drink or a beverage, it may further contain, in addition to the mineral-amino acid complex of the present disclosure, citric acid, fructose syrup, sugar, glucose, acetic acid, malic acid, fruit juice, various plant extracts, etc.

The present disclosure provides a functional health food containing a food composition for enhancing immunological activity, which contains the mineral-amino acid complex as an active ingredient. The functional health food refers to a food prepared by adding the mineral-amino acid complex to a food material such as a beverage, a tea, a spice, a gum, confectionery, etc. and preparing into a capsule, a powder, a suspension, etc., which provides specific health benefit. Because it is prepared from food materials unlike general pharmaceuticals, it has no side effects that may occur when pharmaceuticals are taken for a long time. The functional health food of the present disclosure is very useful because it can be taken every day. The addition amount of the mineral-amino acid complex in the functional health food varies depending on the type of the functional health food, but may be within a range not spoiling the original taste of the food. The addition amount is usually 0.01-50 wt %, specifically 0.1-20 wt %, based on the weight of the food. For a functional health food in the form of a pill, a granule, a tablet or a capsule, the addition amount may be usually 0.1-100 wt %, specifically 0.5-80 wt %. In a specific exemplary embodiment, the functional health food of the present disclosure may be in the form of a pill, a tablet, a capsule or a beverage.

The feed additive composition of the present disclosure may be prepared by adding 0.01-1 wt % of the feed additive composition to a livestock feed composition for pig, chicken, duck, cow, sheep, goat, dog, etc. based on solid contents. It may be administered to various animals. More specifically, it is used as an additive of pig feed.

The feed additive composition of the present disclosure may be prepared into a fermented feed, a mixed feed, a pellet feed, a silage, etc., although not being limited thereto.

MODE FOR INVENTION

Hereinafter, the present disclosure will be described in more detail through examples, etc. However, the scope and contents of the present disclosure should not be interpreted as being limited by the examples, etc. In addition, it is obvious that those of ordinary skill can easily carry out the present disclosure for the matters specific experimental results of which are not provided, based on the description of the present disclosure including the examples, and that such changes and modifications belong to the scope of the appended claims.

Example 1-1: Preparation of Zinc-Aspartic Acid Complex (Using Zinc Sulfate)

After adding 60 g of aspartic acid to 500 mL of water and then adding zinc sulfate (zinc 35 wt %) under stirring, the mixture was reacted sufficiently at 60° C. for 30 minutes or longer under stirring. After centrifugation, about 70 g of a water-soluble zinc-aspartic acid complex was obtained by freeze-drying the supernatant. The zinc sulfate and the aspartic acid were added at a molar ratio of 1:2.

Comparative Example 1-1: Preparation of Zinc-Glutamic Acid Complex (Using Zinc Sulfate)

After adding 60 g of glutamic acid to 500 mL of water and then adding zinc sulfate (zinc 35 wt %) under stirring, the mixture was reacted sufficiently at 50-100° C. for 30 minutes or longer under stirring. After centrifugation, about 70 g of a water-soluble zinc-glutamic acid complex was obtained by freeze-drying the supernatant. The zinc sulfate and the glutamic acid were added at a molar ratio of 1:2.

Comparative Example 1-2: Preparation of Iron-Aspartic Acid Complex (Using Ferrous Lactate)

After adding 60 g of aspartic acid to 500 mL of water and then adding ferrous lactate (iron 35 wt %) under stirring, the mixture was reacted sufficiently at 50-100° C. for 30 minutes or longer under stirring. After centrifugation, about 70 g of a ferrous lactate-aspartic acid complex was obtained by freeze-drying the supernatant. The ferrous sulfate and the aspartic acid were added at a molar ratio of 1:2.

Experimental Example 1: Evaluation of Reaction Yield

The reaction yield of Examples 1-1 and 1-2 and Comparative Examples 1-1 and 1-2 is compared in Table 1. The reaction yield was calculated by analyzing the content of the mineral in the prepared mineral-amino acid complex by ICP assay and dividing it by the theoretical mineral (zinc or iron) content of the added mineral precursor.

TABLE 1

| | Example 1-1 | Example 1-2 | Comparative Example 1-1 | Comparative Example 1-2 |
|---|---|---|---|---|
| Reaction yield (%) | 100% | 100% | 48% | 60% |

As a result, for Examples 1-1 and 1-2, the water-soluble zinc-aspartic acid complexes were prepared with a reaction yield of 100%. In contrast, for Comparative Example 1-1 wherein glutamic acid was used, the reaction yield was very low as about 50% or below because glutamic acid was not completely dissolved in water. Also, for Comparative Example 1-2, wherein ferrous lactate was used, the reaction yield was very low as about 60%.

Example 2-1: Preparation of Feed Additive Composition

After adding 100 parts by weight of rice bran to 20 parts by weight of the zinc-aspartic acid complex of Example 1-1 and mixing the same, a feed additive composition in the form of a fine powder was prepared by drying the mixture in a desiccator at 80° C. to a water content of 10% or lower and then pulverizing with a roll mill grinder.

Comparative Example 2-1: Preparation of Feed Additive Composition

A feed additive composition was prepared in the same manner as in Example 2-1, except for using the zinc-glutamic acid complex of Comparative Example 1-1 instead of the zinc-aspartic acid complex of Example 1-1.

Comparative Example 2-2: Preparation of Feed Additive Composition

A feed additive composition was prepared in the same manner as in Example 2-1, except for using the ferrous lactate-aspartic acid complex of Comparative Example 1-2 instead of the zinc-aspartic acid complex of Example 1-1.

Experimental Example 2: Evaluation of Feed Efficiency and Malodorous Materials in Manure In order to investigate the feed efficiency of the feed additive compositions and their effect on the growth of pig, the feed additive composition of Example 2-1, Comparative Example 2-1 or Comparative Example 2-2 was fed to pigs after being mixed with pig feed at 0.2 wt %. The result is given in Table 2.

TABLE 2

| | Example 2-1 | Comparative Example 2-1 | Comparative Example 2-2 |
|---|---|---|---|
| Number of heads | 30 | 30 | 30 |
| Feed intake | 223 kg | 285 kg | 281 kg |
| Duration to reach 110 kg | 160.7 days | 189.8 days | 181.1 days |

As seen from Table 2, when the feed additive composition of Example 2-1 was added to pig feed, the duration to reach 110 kg was reduced by about 20 days and, accordingly, the feed intake was decreased by about 20.7%. In addition, for analysis of the generation of ammonia and hydrogen sulfide, which are associated with malodor, from pig manure, 100 g of fresh manure was collected at the end of the experiment in a specially prepared plastic container and the concentration of generated ammonia and hydrogen sulfide was measured at room temperature with the lapse of time (3 hours and 24 hours later) using a digital gas analyzer (Multi Gas Monitor PGM-7800, RAE Systems Inc., USA). The result is shown in Table 3.

TABLE 3

| | Ammonia | | Hydrogen sulfide | |
|---|---|---|---|---|
| Unit: ppm | 3 hours | 24 hours | 3 hours | 24 hours |
| Example 2-1 | 4.3 | 20.5 | 28.1 | 3.8 |
| Comparative Example 2-1 | 4.5 | 45.5 | 38.8 | 4.2 |
| Comparative Example 2-2 | 4.4 | 35.8 | 45.5 | 6.3 |

As seen from Table 3, the concentration of ammonia and hydrogen sulfide in the malodorous gas generated from manure was remarkably lower for Example 2-1, as compared to Comparative Examples 2-1 and 2-2.

Example 1-2: Preparation of Zinc-Aspartic Acid Complex (Using Zinc Oxide)

After adding 57.5 g of aspartic acid to 500 mL of water and then adding 17.5 g of zinc sulfate (zinc 81 wt %) under stirring, the mixture was reacted sufficiently at 90° C. for 120 minutes or longer under stirring. After filtering the reaction solution through 0.2-μm filter paper, the filtrate was concentrated to 80% at 65° C. for 3 hours, and a water-soluble zinc-aspartic acid complex was obtained by drying in vacuo.

Experimental Example 3: Identification of Structure of Zinc-Aspartic Acid Complex The structure of the zinc-aspartic acid complex of Example 1-2 was identified using the Bruker SMART APEX II X-ray crystallography (XRC) system and the Bruker SHELXTL structure analysis program.

| Crystallographic data | |
|---|---|
| Molecular formula | $C_4H_9NO_7Zn$ |
| Molecular weight | 248.49 |
| Crystal system | orthorhombic |
| Space group | P2(1)2(1)2(1) |
| Z | 4 |
| Unit cell dimension | a = 7.8012(15) Å α = 90°<br>b = 9.3435(17) Å β = 90°<br>c = 11.576(2) Å γ = 90° |

-continued

| Crystallographic data | |
|---|---|
| Volume | 843.8(3)/Å$^3$ |
| Calculated density | 1.956 Mg/m$^3$ |
| Temperature | 296(1) K. |
| Absolute structural parameter | 0.00 |
| Crystal size | 0.18 × 0.12 × 0.08 mm$^3$ |
| F(000) | 504 |
| Absorption coefficient | 2.920 mm$^{-1}$ |

Table 4 shows atomic coordinates (×10$^4$) and equivalent isotropic displacement parameters (Å$^2$×10$^3$). U (eq) is defined as ⅓ of the trace of the orthogonalized $U_{ij}$ tensor.

TABLE 4

| | x | y | z | U(eq) |
|---|---|---|---|---|
| Zn(1) | 1142 (1) | 2951 (1) | 6577 (1) | 21 (1) |
| O(1) | 705 (3) | 4950 (2) | 7471 (2) | 24 (1) |
| O(2) | 1222 (3) | 7202 (2) | 7956 (2) | 26 (1) |
| O(3) | 422 (3) | 5986 (3) | 4052 (2) | 35 (1) |
| O(4) | −32 (3) | 4009 (3) | 5078 (2) | 27 (1) |
| O(5) | 1555 (4) | 923 (3) | 5733 (2) | 27 (1) |
| N(1) | 3232 (4) | 3849 (3) | 5768 (2) | 23 (1) |
| O(6) | 2239 (4) | 2184 (3) | 8104 (2) | 31 (1) |
| C(1) | 1405 (4) | 6121 (3) | 7298 (3) | 19 (1) |
| C(2) | 2605 (4) | 6362 (3) | 6273 (3) | 25 (1) |
| C(3) | 2643 (4) | 5233 (3) | 5317 (3) | 21 (1) |
| C(4) | 870 (4) | 5048 (3) | 4773 (3) | 21 (1) |
| O(7) | 1464 (4) | 513 (3) | 2877 (2) | 32 (1) |

Table 5 shows bond lengths (ÅA) and angles (°).

TABLE 5

| | |
|---|---|
| Zn(1)—O(2)#1 | 2.045 (2) |
| Zn(1)—N(1) | 2.059 (3) |
| Zn(1)—O(6) | 2.090 (3) |
| Zn(1)—O(5) | 2.157 (3) |
| Zn(1)—O(1) | 2.162 (2) |
| Zn(1)—O(4) | 2.198 (2) |
| O(1)—C(1) | 1.239 (4) |
| O(2)—C(1) | 1.272 (4) |
| O(2)—Zn(1)#2 | 2.045 (2) |
| O(3)—C(4) | 1.260 (4) |
| O(4)—C(4) | 1.249 (4) |
| O(5)—H(5A) | 0.79 (5) |
| O(5)—H(5B) | 0.71 (6) |
| N(1)—C(3) | 1.468 (4) |
| N(1)—H(1A) | 0.8600 |
| N(1)—H(1B) | 0.8600 |
| O(6)—II(6A) | 0.71 (6) |
| O(6)—H(6B) | 0.98 (5) |
| C(1)—C(2) | 1.528 (4) |
| C(2)—C(3) | 1.530 (4) |
| C(2)—H(2A) | 0.9700 |
| C(2)—H(2B) | 0.9700 |
| C(3)—C(4) | 1.529 (4) |
| C(3)—H(3B) | 0.9800 |
| O(2)#1—Zn(1)—N(1) | 166.82 (10) |
| O(2)#1—Zn(1)—O(6) | 91.62 (11) |
| N(1)—Zn(1)—O(6) | 101.55 (12) |
| O(2)#1—Zn(1)—O(5) | 87.35 (11) |
| N(1)—Zn(1)—O(5) | 91.91 (12) |
| O(6)—Zn(1)—O(5) | 91.20 (10) |
| O(2)#1—Zn(1)—O(1) | 91.56 (9) |
| N(1)—Zn(1)—O(1) | 89.46 (10) |
| O(6)—ZN(1)—O(1) | 87.50 (10) |
| O(5)—ZN(1)—O(1) | 178.28 (11) |
| O(2)#1—Zn(1)—O(4) | 89.25 (9) |
| N(1)—Zn(1)—O(4) | 77.72 (10) |
| O(6)—Zn(1)—O(4) | 173.08 (10) |
| O(5)—Zn(1)—O(4) | 95.70 (10) |
| O(1)—ZN(1)—O(4) | 85.61 (9) |
| C(1)—O(1)—Zn(1) | 128.1 (2) |

TABLE 5-continued

| | |
|---|---|
| C(1)—O(2)—Zn(1)#2 | 122.1 (2) |
| C(4)—O(4)—Zn(1) | 109.7 (2) |
| Zn(1)—O(5)—H(5A) | 96 (3) |
| Zn(1)—O(5)—H(5B) | 114 (5) |
| H(5A)—O(5)—H(5B) | 125 (6) |
| C(3)—N(1)—Zn(1) | 105.81 (19) |
| C(3)—N(1)—H(1A) | 1200 |
| Zn(1)N(1)—H(1A) | 73.4 |
| C(3)—N(1)—H(1B) | 120.0 |
| Zn(1)—N(1)—H(1B) | 90.7 |
| H(1A)—N(1)—H(1B) | 120.0 |
| Zn(1)—O(6)—H(6A) | 115 (4) |
| Zn(1)—O(6)—H(6B) | 117 (2) |
| H(6A)—O(6)—H(6B) | 108 (5) |
| O(1)—C(1)—O(2) | 123.7 (3) |
| O(1)—C(1)—C(2) | 121.7 (3) |
| O(2)—C(1)—C(2) | 114.6 (3) |
| C(1)—C(2)—C(3) | 118.2 (3) |
| C(1)—C(2)—H(2A) | 107.8 |
| C(3)—C(2)—H(2A) | 107.8 |
| C(1)—C(2)—H(2B) | 107.8 |
| C(3)—C(2)—II(2B) | 107.8 |
| H(2A)—C(2)—H(2B) | 107.1 |
| N(1)—C(3)—C(2) | 110.9 (3) |
| N(1)—C(3)—C(4) | 109.3 (2) |
| C(2)—C(3)—C(4) | 111.0 (3) |
| N(1)—C(3)—H(3B) | 108.5 |
| C(2)—C(3)—H(3B) | 108.5 |
| C(4)—C(3)—H(3B) | 108.5 |
| O(4)—C(4)—O(3) | 124.8 (3) |
| O(4)—C(4)—C(3) | 118.8 (3) |
| O(3)—C(4)—C(3) | 116.4 (3) |

Symmetric transformation was used to generate equivalent atoms (#1−x, y−1/2, −z+3/2; #2−x, y+1/2, −z+3/2).

Table 6 shows anisotropic displacement parameters (Å$^2$×10$^3$). The anisotropic displacement factor exponent takes the form of $-2\pi^2[h^2a^{*2}U^{11}+ \ldots +2hka^*b^*U^{12}]$.

TABLE 6

| | $U^{11}$ | $U^{22}$ | $U^{33}$ | $U^{23}$ | $U^{13}$ | $U^{12}$ |
|---|---|---|---|---|---|---|
| Zn(1) | 21 (1) | 18 (1) | 23 (1) | 1 (1) | 1 (1) | −1 (1) |
| O(1) | 27 (1) | 18 (1) | 28 (1) | −3 (1) | 8 (1) | −2 (1) |
| O(2) | 20 (1) | 21 (1) | 37 (1) | −10 (1) | 5 (1) | 0 (1) |
| O(3) | 34 (1) | 34 (1) | 37 (1) | 15 (1) | −7 (1) | −2 (1) |
| O(4) | 22 (1) | 28 (1) | 31 (1) | 5 (1) | −6 (1) | −6 (1) |
| O(5) | 28 (2) | 26 (1) | 27 (1) | −2 (1) | 2 (1) | 3 (1) |
| N(1) | 22 (1) | 23 (1) | 24 (1) | −1 (1) | 1 (1) | 2 (1) |
| O(6) | 40 (1) | 23 (1) | 30 (1) | −4 (1) | −11 (1) | 0 (1) |
| C(1) | 15 (1) | 16 (1) | 25 (1) | −2 (1) | −1 (1) | 2 (1) |
| C(2) | 25 (2) | 21 (2) | 29 (2) | −2 (1) | 3 (1) | −3 (1) |
| C(3) | 20 (1) | 21 (2) | 23 (1) | −1 (1) | 4 (1) | −2 (1) |
| C(4) | 22 (2) | 22 (1) | 19 (1) | 1 (1) | 1 (1) | 2 (1) |
| O(7) | 33 (1) | 27 (1) | 37 (1) | 0 (1) | −1 (1) | −1 (1) |

Table 7 shows hydrogen coordinates (×10$^4$) and equivalent isotropic displacement parameters (Å$^2$×10$^3$).

TABLE 7

| | x | y | z | U(eq) |
|---|---|---|---|---|
| H(5A) | 1200 (60) | 450 (50) | 6250 (40) | 26 (11) |
| H(5B) | 2380 (80) | 850 (60) | 5490 (50) | 43 (16) |
| H(1A) | 3499 | 3765 | 6486 | 27 |
| H(1B) | 3311 | 3123 | 5315 | 27 |
| H(6A) | 2870 (70) | 2640 (50) | 8360 (40) | 33 (13) |
| H(6B) | 2700 (60) | 1210 (50) | 8100 (30) | 28 (10) |
| H(2A) | 3760 | 6459 | 6573 | 30 |
| H(2B) | 2302 | 7271 | 5922 | 30 |
| H(3B) | 3443 | 5548 | 4716 | 25 |

Table 8 shows torsion angles (°).

TABLE 8

| | |
|---|---|
| O(2)#1—Zn(1)—O(1)—C(1) | −157.2 (3) |
| N(1)—Zn(1)—O(1)—C(1) | 9.7 (3) |
| O(6)—Zn(1)—O(1)—C(1) | 111.3 (3) |
| O(5)—Zn(1)—O(1)—C(1) | 152 (3) |
| O(4)—Zn(1)—O(1)—C(1) | −68.0 (3) |
| O(2)#1—Zn(1)—O(4)—C(4) | 154.9 (2) |
| N(1)—Zn(1)—O(4)—C(4) | −27.1 (2) |
| O(6)—Zn(1)—O(4)—C(4) | 57.6 (10) |
| O(5)—Zn(1)—O(4)—C(4) | −117.8 (2) |
| O(1)—Zn(1)—O(4)—C(4) | 63.3 (2) |
| O(2)#1—Zn(1)—N(1)—C(3) | 46.0 (5) |
| O(6)—Zn(1)—N(1)—C(3) | −135.85 (19) |
| O(5)—Zn(1)—N(1)—C(3) | 132.54 (19) |
| O(1)—Zn(1)—N(1)—C(3) | −48.5 (2) |
| O(4)—Zn(1)—N(1)—C(3) | 37.11 (19) |
| Zn(1)—O(1)—C(1)—O(2) | −171.1 (2) |
| Zn(1)—O(1)—C(1)—C(2) | 7.5 (4) |
| Zn(1)#2—O(2)—C(1)—O(1) | −52.2 (4) |
| Zn(1)#2—O(2)—C(1)—C(2) | 129.1 (2) |
| O(1)—C(1)—C(2)—C(3) | 12.6 (5) |
| O(2)—C(1)—C(2)—C(3) | −168.7 (3) |
| Zn(1)—N(1)—C(3)—C(2) | 79.7 (3) |
| Zn(1)—N(1)—C(3)—C(4) | −42.9 (3) |
| C(1)—C(2)—C(3)—N(1) | −62.3 (4) |
| C(1)—C(2)—C(3)—C(4) | 59.3 (4) |
| Zn(1)—O(4)—C(4)—O(3) | −169.3 (3) |
| Zn(1)—O(4)—C(4)—C(3) | 9.7 (3) |
| N(1)—C(3)—C(4)—O(4) | 22.1 (4) |
| C(2)—C(3)—C(4)—O(4) | −100.5 (3) |
| N(1)—C(3)—C(4)—O(3) | −158.8 (3) |
| C(2)—C(3)—C(4)—O(3) | 78.6 (3) |

From the above results, the water-soluble zinc-aspartic acid complex of Example 2-1 was identified as zinc aspartate hydrate of Chemical Formula 1 having a molecular formula $C_4H_9NO_7Zn$.

[Chemical Formula 1]

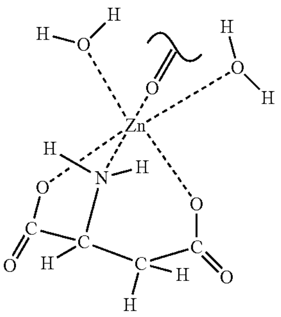

The zinc aspartate hydrate of Chemical Formula 1 was identified as a novel zinc aspartate hydrate having a total of six coordinate bonds, with two water molecules, two oxygen atoms of first aspartic acid, one nitrogen atom of the amino group of the first aspartic acid, and one oxygen atom of second aspartic acid coordinate-bonded to zinc, wherein zinc and aspartic acid are bonded at a molar ratio of 1:1.

FIG. 1 schematically shows the coordinate bonding of aspartic acid (second aspartic acid) in the zinc aspartate hydrate of Chemical Formula 1 with neighboring zinc aspartate hydrate.

Comparative Example 3: Commercially Available Zinc-Aspartic Acid Complex

A feed additive composition was prepared using a (water-insoluble) complex with a molecular formula of $C_8H_{10}N_2O_8Zn.2H$ and a molecular weight 329.58, wherein zinc and aspartic acid are bonded at a molar ratio of 1:2.

Experimental Example 4: Antibody Titer Against Foot-and-Mouth Disease of Pig

In order to investigate the effect of the feed additive composition on the blood and antibody titer against foot-and-mouth disease of pigs, animal experiments were conducted for 6 weeks by adding zinc oxide powder, zinc sulfate powder, the zinc-aspartic acid complex of Example 1-1 (using zinc sulfate), the zinc-aspartic acid complex of Example 1-2 (using zinc oxide) or the zinc-aspartic acid complex of Comparative Example 3 to feed. The body weight of pigs at the start of the experiment was 25.56±2.22 kg.

Corn-soybean meal feed prepared according to the NRC (2012) requirement was used. After adding 0.1 wt % of zinc oxide powder (CON 1), 0.3 wt % of zinc sulfate powder (CON 2), 0.3 wt % of the zinc-aspartic acid complex of Example 1-1 (Example 1-1-0.3), 0.1 wt % of the zinc-aspartic acid complex of Example 1-2 (Example 1-2-0.1), 0.3 wt % of the zinc-aspartic acid complex of Example 1-2 (Example 1-2-0.3) or 0.3 wt % of the zinc-aspartic acid complex of Comparative Example 3 (Comparative Example 3-0.3) to the feed, the feed was randomly given to 240 crossbred (Duroc×Yorkshire×Landrace) pigs 4 times, 8 per each treatment (n=5 each). Free access was allowed to the feed and water was given freely using an automatic water supplier.

1) Body Weight Change

Body weight was measured at the start and end of the feeding. The change in body weight is shown in Table 9.

TABLE 9

| | CON 1 | CON 2 | Example 1-1-0.3 | Example 1-2-0.1 | Example 1-2-0.3 | Comparative Example 3-0.3 |
|---|---|---|---|---|---|---|
| Start time | 22.56 | 22.56 | 22.56 | 22.56 | 22.56 | 22.56 |
| End time | 53.62b | 53.74b | 54.43ab | 55.40a | 54.76ab | 54.55a |

For 6 weeks, although no remarkable change in body weight was observed, Example 1-1-0.3, Example 1-2-0.1, Example 1-2-0.3 and Comparative Example 3-0.3 showed slight increase in body weight as compared to CON 1 and CON 2.

2) Contents of Zinc and Immunoglobulin in Blood

At the end of the experiment (6 weeks), 5 mL of blood was taken from the jugular vein using an E3 EDTA vacuum tube (Becton Dickinson Vacutainer Systems, Granklin Lakes, NJ). After centrifugation at 4° C. and 3000 rpm for 15 minutes, the contents of zinc and immunoglobulin in serum were measured. The result is shown in Table 10.

TABLE 10

| | CON 1 | CON 2 | Example 1-1-0.3 | Example 1-2-0.1 | Example 1-2-0.3 | Comparative Example 3-0.3 |
|---|---|---|---|---|---|---|
| Zinc (μg/dL) | 100c | 98c | 158b | 177ab | 205a | 180ab |
| IgG (mg/dL) | 472b | 466b | 480b | 504ab | 546a | 489b |

For Example 1-1-0.3, Example 1-2-0.1, Example 1-2-0.3 and Comparative Example 3-0.3, the zinc content in blood was increased significantly as compared to CON 1 and CON 2. In particular, the higher zinc content in blood for Example 1-1-0.3, Example 1-2-0.3 and Comparative Example 3-0.3 despite the higher zinc feeding for CON 1 and CON 2 confirms the high bioavailability of the mineral-amino acid complex of the present disclosure and the zinc-aspartic acid complex of Comparative Example 3. The immunoglobulin content in blood for Example 1-1-0.3 and Comparative Example 3-0.3 was not significantly different from CON 1 and CON 2, but significant increase was observed for Example 1-2-0.3. Especially, Example 1-2-0.1 wherein the administration dosage was reduced to 1/3 also showed distinct, although not significant, increase.

3) Production of Foot-and-Mouth Disease Antibody

Foot-and-mouth disease antibody (FMDV type 0) in the serum obtained in 2) of Experimental Example 3 was analyzed. The duration of antibody and the antibody production with time after vaccination were investigated by analyzing percentage inhibition titer (PI) by SP ELISA. The result was tested by simple linear regression analysis. The SP antibody examination was conducted using a Prio-CHECK FMDV type 0 ELISA kit (Prionics Lelystad B. V., the Netherlands) according to the manufacturer's instructions. After calculating the PI value from the formula $\{100-(\text{corrected } OD_{450} \text{ test sample/corrected } OD_{450} \text{ max})\times 100\}$, the result was evaluated as positive if the PI was 50 or higher, and as negative if the PI was below 50.

TABLE 11

| | CON 1 | CON 2 | Example 1-1-0.3 | Example 1-2-0.1 | Example 1-2-0.3 | Comparative Example 3-0.3 |
|---|---|---|---|---|---|---|
| Antibody titer (PI) | 47.38b | 47.52b | 51.88b | 55.65b | 78.07a | 54.45b |
| Positive rate | 50 | 50 | 75 | 100 | 100 | 75 |

The production of the foot-and-mouth disease antibody was increased slightly for Example 1-1-0.3, Example 1-2-0.1 and Comparative Example 3-0.3 as compared to CON 1 and CON 2, but there was no significant difference. Significant increase as compared to CON 1 and CON 2 was observed only for Example 1-2-0.3. Whereas the positive rate for the foot-and-mouth disease antibody was 50% for CON 1 and CON 2, it was 75% for Example 1-1-0.3 and Comparative Example 3-0.3, and 100% for Example 1-2-0.1 and Example 1-2-0.3.

All the data for Experimental Example 3 were analyzed by linear, quadratic, cubic analysis using the general linear model procedure of SAS (2013). The difference in average values was tested by Duncan's multiple range test and significance was determined at $P<0.05$.

Experimental Example 5: Inhibitory effect against influenza H1N1

12-week-old female (ICR) mice (Orient Bio Inc., Seoul, Korea) weighing 29±1 g were used for experiment. Prior to the experiment, the mice were accustomed to the experimental environment for 7 days. During the accustomization period, the mice were kept in cages controlled to 22±1° C. and 55±10% humidity. Feed was allowed freely and lighting was controlled with 12-hour cycles.

The mice were divided into a virus control group, CON 1, Example 1-1, Example 1-2 and Comparative Example 3, n=10 per each group. After administering H1N1 virus to each group, each sample diluted in physiological saline was orally administered at 20 µg/kg/day for 5 days. Physiological saline was administered to a negative control group, and the virus control group was infected with virus but was not administered with a sample.

1) Change in Body Weight

Body weight was measured at the start and end of the experiment. The change in body weight is shown in Table 12.

TABLE 12

| | Negative control | Virus control | CON 2 | Example 1-1 | Example 1-2 | Comparative Example3 |
|---|---|---|---|---|---|---|
| Start point (day 0) | 100.0 | 100.0 | 100.0 | 100.0 | 100.0 | 100.0 |
| End point (day 5) | 106.0b | 99.1a | 99.9a | 104.8ab | 106.8b | 103.7ab |

After the administration of virus, the virus control group and CON 2 showed decreased body weight as compared to the negative control group. However, Example 1-1, Example 1-2 and Comparative Example 3 did not show significant increase in body weight as compared to the negative control group.

2) H1N1 Virus Content in Lung Tissue

After sacrificing the mice, the content of the virus existing in lung tissue was determined by measuring titer. The result is shown in Table 13.

TABLE 13

| | Negative control | Virus control | CON 2 | Example 1-1 | Example 1-2 | Comparative Example 3 |
|---|---|---|---|---|---|---|
| Tissues virus titers ($Log_{10}$ $TCID_{50}$) | 0.0a | 5.2b | 4.4b | 4.1b | 2.1a | 3.9b |

It was confirmed that the virus content in the lung tissue was decreased significantly only in Example 1-2.

I claim:

1. A method of increasing antibody titer against foot-and-mouth disease or decreasing avian influenza virus titer in an animal in need thereof, comprising administering to the animal in need thereof an effective amount of an amino acid-mineral complex as an active ingredient, wherein the amino acid-mineral complex is a water-soluble zinc aspartate hydrate of Chemical Formula 1 having a molecular formula $C_4H_9NO_7Zn$:

[Chemical Formula 1]

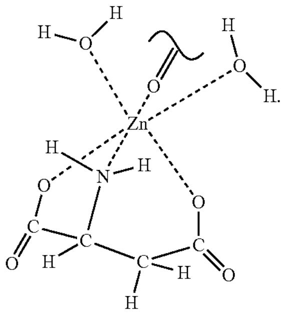

wherein the avian influenza is H1N1;

wherein the amino acid-mineral complex is comprised in a feed additive composition at a concentration between 0.1 wt % to 0.3 wt %; or the animal in need thereof is administered 20 μg/kg/day of the amino acid-mineral complex.

2. The method according to claim 1, wherein the amino acid-mineral complex is comprised in a food composition, a food additive composition, a pharmaceutical composition, a feed composition or a feed additive composition.

3. The method according to claim 1, comprising increasing antibody titer against foot-and-mouth disease.

4. The method according to claim 1, comprising decreasing avian influenza virus titer.

5. The method according to claim 3, wherein the amino acid-mineral complex is comprised in a feed additive composition at a concentration between 0.1 wt % to 0.3 wt %.

6. The method according to claim 4, comprising administering to the animal in need thereof 20 μg/kg/day of the amino acid-mineral complex.

* * * * *